US00PP11294P

United States Patent [19]

Boeder

[11] Patent Number: Plant 11,294

[45] Date of Patent: Mar. 14, 2000

[54] CHRYSANTHEMUM PLANT NAMED 'CLEAGAR CKT'

[75] Inventor: Mark Boeder, West Wittering, United Kingdom

[73] Assignee: Cleangro Limited, West Sussex, United Kingdom

[21] Appl. No.: 09/038,793

[22] Filed: Mar. 11, 1998

[51] Int. Cl.[7] ..... A01H 5/00

[52] U.S. Cl. ..... Plt./294

[58] Field of Search ..... Plt./294

[56] References Cited

U.S. PATENT DOCUMENTS

| | | | |
|---|---|---|---|
| P.P. 1,171 | 2/1953 | Boerner | Plt./289 |
| P.P. 8,609 | 2/1994 | VandenBerg | Plt./294 |
| P.P. 8,806 | 6/1994 | Polys | Plt./294 |

OTHER PUBLICATIONS

UPOUROM, 1999/02, Plant Variety Database, GTI Jouve Retrieval Software, citation for 'Cockatoo'.

*Primary Examiner*—Howard J. Locker
*Attorney, Agent, or Firm*—Christie, Parker & Hale, LLP

[57] ABSTRACT

A garden type Chrysanthemum plant with daisy-type flowers having white ray florets and yellow disc florets.

1 Drawing Sheet

BACKGROUND OF THE INVENTION

The present invention is directed to a new and distinct variety of Chrysanthemum botanically classified as *Dendranthema grandiflora*. The varietal denomination of the new chrysanthemum is 'Cleagar CKT'.

The female parent of the new variety is an unnamed, undistributed seedling identified as 'G12-C1' and the male parent is an undistributed, unnamed seedling identified as 'G23-C1'. The new variety has been asexually reproduced by vegetative cuttings in Ventura County, Calif. and the distinguishing characteristics are retained through successive generations of asexual reproduction.

SUMMARY OF THE INVENTION

A garden type Chrysanthemum with daisy type flowers having white ray florets and yellow disc florets.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Cleagar CKT' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Cleagar CKT' is about 21 days with the response time of about 7 weeks. No treatment with growth retardant is required. Useful growing conditions include night temperatures of about 64°–66° F., day temperatures of about 80°–85° F. and about 5,000 foot-candles of light.

Plant:

*Habit.*—Mounding, compact, very round.
*Height.*—About 20 cm.
*Number of breaks from pinch.*—About 4.
*Typical container sizes commercially grown in.*—4 inch, 6 inch, 1 gallon, 3 gallon containers.
*Length of lateral branches.*—About 11 cm.
*Stem color.*—Near 137 D.

Foliage:

*Leaf arrangement.*—Alternate.
*Number of leaves per lateral branch.*—About 12.
*Leaf size.*—Length: About 5.8 cm. Width: About 3.8 cm.
*Leaf shape.*—Ovate.
*Attachment.*—Petioled.
*Leaf apex.*—Acute.
*Base.*—Tapered.
*Margin.*—Lobed, infrequent serrations.
*Aspect.*—Slightly undulating.
*Surface.*—Top: Slightly pubescent. Bottom: Slightly pubescent.
*Petiole.*—Length: About 2.7 cm. Color: Near 137D.
*Color.*—Mature leaf: Top: Near 147A. Bottom: Near 137C. Young leaf: Top: Near 137B. Bottom: Near 137C.

Flower:

*Inflorescence form.*—Cyme.
*Flower form.*—Daisy.
*Number of blooms per branch.*—About 10.
*Diameter of fully expanded bloom.*—About 5.5 cm.
*Diameter of daisy disc.*—About 1.7 cm.
*Depth of fully expanded bloom.*—About 2.1 cm.
*Sepal number.*—About 20. Color: Near 137 A.
*General appearance of sepals.*—Fleshy, pubescent, concave.
*Peduncle.*—Length: Lower most peduncles are about 7 cm, terminal peduncles are about 3 cm. Habit: Slight outward curve. Surface: Pubescent. Strength: Sturdy.
*Flower bud shape.*—Flattened sphere. Diameter: About 1 cm. Height: About 0.6 cm.
*Ray florets.*—Number per flower: About 50. Shape: Oblanceolate. Apex: 3 lobed. Base: Tapered. Margin:

Entire. Aspect: Slightly convex. Length: About 2.7 cm. Width: About 1.0 cm.

*Disc florets.*—Number per flower: About 150. Shape: Cylindrical. Length: About 0.4 cm. Width: About 0.1 cm.

*Fragrance.*—Moderate.

Flower Color:

*General flower coloration.*—Clear white daisy with a dark yellow disc.

*Ray florets, top side.*—Immature: Near 155D. Mature: Near 155D. Fading: Near 155D.

*Ray floret, under side.*—Immature: Near 155D. Mature: Near 155D. Fading: Near 155D.

*Disc florets.*—Immature: Near 154B. Mature: Near 15A. Fading: Near 17C.

*Changes as the flower ages.*—Flowers take on a dull yellow-orange appearance.

Reproductive organs:

*Ray florets.*—Pistillate. Stigma shape: Two branched. Stigma color: Near 8A. Style length: About 0.4cm.

*Disc florets.*—Stigma shape: Two branched, curled. Stigma color: Near 9A. Style length: About 0.4 cm.

*Disc florets.*—Stigma shape: Two branched, curled. Stigma color: Near 9A. Style length: About 0.4 cm. Stamen number: About 5. Anther length: About 0.2 cm. Pollen color: Near 16A. Pollen quantity: Abundant.

What is claimed is:

1. A new and distinct Chrysanthemum plant of the variety substantially as herein shown and described.

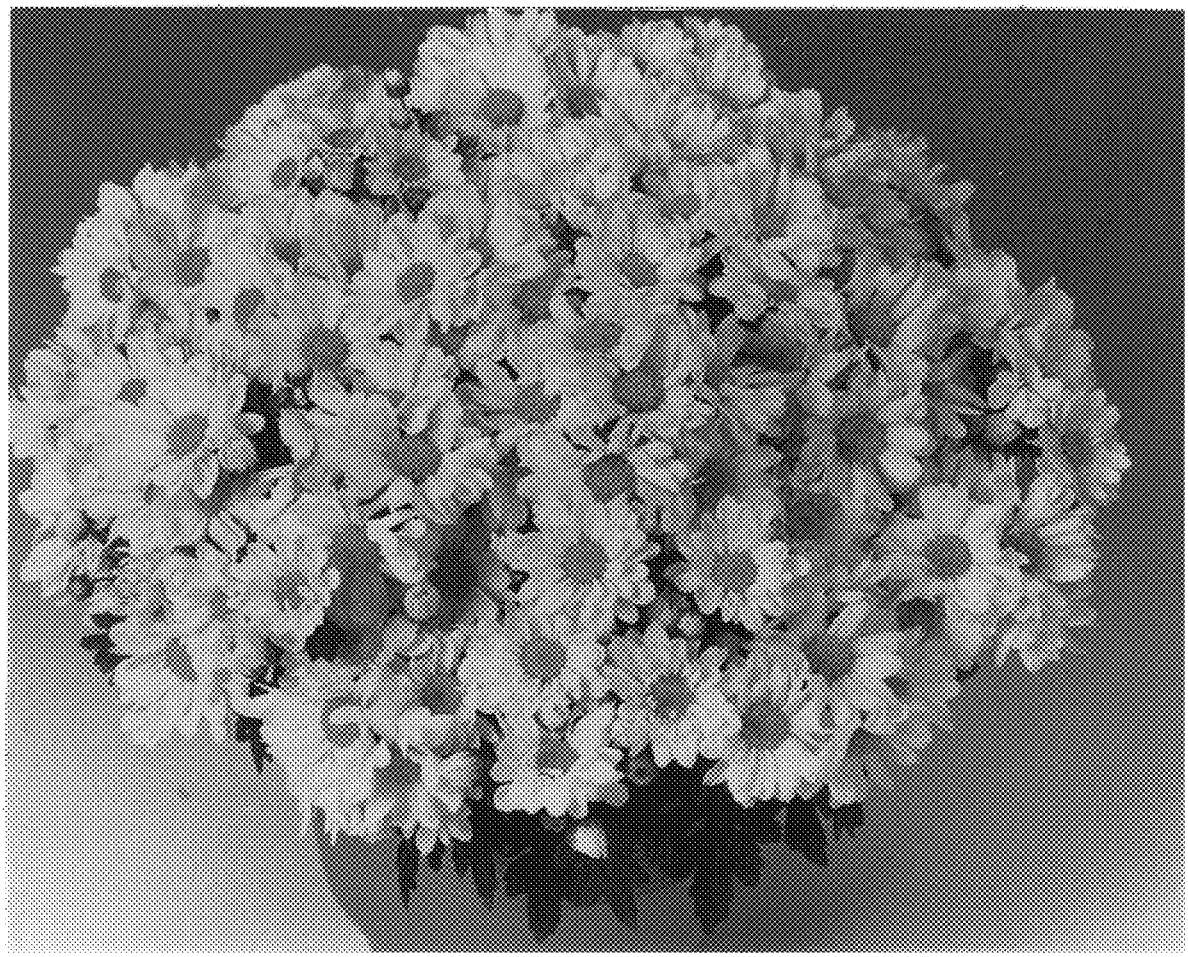

* * * * *